(12) United States Patent
Meng

(10) Patent No.: US 8,565,376 B2
(45) Date of Patent: Oct. 22, 2013

(54) METHOD AND APPARATUS FOR MEASURING PROPERTIES OF A COMPOUND

(75) Inventor: Ling Jian Meng, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 435 days.

(21) Appl. No.: 12/986,160

(22) Filed: Jan. 6, 2011

(65) Prior Publication Data

US 2011/0188629 A1 Aug. 4, 2011

Related U.S. Application Data

(60) Provisional application No. 61/293,118, filed on Jan. 7, 2010.

(51) Int. Cl.
*G01N 23/223* (2006.01)
*G01T 1/36* (2006.01)
*G21K 1/02* (2006.01)

(52) U.S. Cl.
USPC ............................. 378/45; 378/49; 378/148

(58) Field of Classification Search
USPC ......... 378/44–46, 48, 49, 147, 148, 149, 210; 250/370.01, 370.08, 370.09
See application file for complete search history.

(56) References Cited

U.S. PATENT DOCUMENTS 5,408,512 A * 4/1995 Kuwabara et al. ............. 378/45
7,120,226 B2 * 10/2006 Ledoux et al. ................. 378/57
7,649,975 B2 * 1/2010 Boyden et al. ................. 378/45

OTHER PUBLICATIONS

Agostinelli et al, "GEANT4—a simulation toolkit", Nuclear Instrument and Methods in Physics Research A 506 (2003) 250-303.
Allison et al, "Geant4 Developments and Applications", IEEE Transactions on Nuclear Science, vol. 53, No. 1, Feb. 2006.
Chukalina et al, "Quantitative comparison of X-ray fluorescence microtomography setups: Standard and confocal collimator apparatus", Spectrochimica Acta Part H 62 (2001) 544-548.
Chukalina et al, "X-ray fluorescence tomography for non-destructive semi-quantitative study of microobjects", J. Phys. IV France 104 (2003).
Fessler et al, "Spatial Resolution Properties of Penalized-Likelihood Image Reconstruction: Space-Invariant Tomographs", IEEI:'. Tilansaciions on Image Processing. vol. 5, No. 9. Sep. 1996.

(Continued)

*Primary Examiner* — Anastasia Midkiff
(74) *Attorney, Agent, or Firm* — Guntin & Gust, PLC; Ed Guntin

(57) ABSTRACT

A system that incorporates teachings of the present disclosure may include, for example, an apparatus having a collimator having at least one aperture and a fluorescence detector. The collimator can be positioned next to a compound. The compound can emit fluorescence X-rays when impacted by an X-ray beam generated by an X-ray source. The collimator can absorb at least a first portion of the fluorescence X-rays emitted by the compound and release at least a second portion of the fluorescence X-rays at the at least one aperture. The second portion of the fluorescence X-rays released by the at least one aperture have known directional information based on a position of the collimator. The fluorescence detector can detect the second portion of the fluorescence X-rays released by the at least one aperture. A three-dimensional (3-D) rendering of an elemental distribution of the compound can be determined from the fluorescence X-rays detected and the directional information. Additional embodiments are disclosed.

20 Claims, 13 Drawing Sheets

(56) References Cited

OTHER PUBLICATIONS

Hansson et al, "In vivo x-ray fluorescence analysis (XRF) of the thyroid iodine content—Influence of measurement geometries on the iodine Ka signal", X-Ray Spectrometry, X-Ray Spectrom, 2008; 37: 37-41, Published online Sep. 14, 2007 in Wiley InteScience.

Hasegawa et al, "Improvement of Imaging Speed in Fluorescent X-Ray Computed Tomography Using Synchrotron Radiation", Systems and Computers in Japan. vol. 33. No. 2. 2002.

La Riviere et al, "Reduced-Scan Schemes for X-Ray Fluorescence Computed Tomography", IEEE Transactions on Nuclear Science. vol. 54. No. 5. Oct. 2007.

Meng et al, "A Modified Uniform Cramer-Rao Bound for Multiple Pinhole Aperture Design", IEEE Transactions on Medical Imaging. vol. 23. No. 7. Jul. 2004.

Meng et al, "Feasibility Study of Using Hybrid Collimation for Nuclear Environmental Imaging", IEEE Transactions on Nuclear Science. vol. SO, No. 4, Aug. 2003.

Meng et al, "Design and Feasibility Study of a Single Photon Emission Microscope System for Small Animal 1-125 Imaging", IEEE Transactions on Nuclear Science. vol. 53. No. 3.Jun. 2006.

Meng et al, "Feasibility Study of Compton Scattering Enchanced Multiple Pinhole Imager for Nuclear Medicine", IEEE Transactions on Nuclear Science. vol. 50, No. 5, Oct. 2003.

Pereira et al, "Computed tomography and X-ray fluorescence CT of biological samples", Nuclear Instruments and Methods in Physics Research A 580 (2007) 951-954.

Takeda, "Phase-contrast and fluorescent X-ray imaging for biomedical researches", Nuclear Instruments and Methods in Physics Research A 548 (2005) 38-46.

Takeda et al, "Fluorescent Scanning X-Ray Tomographic Image with Monochromatic Synchrotron X -Ray", Medical Imaging Technology vol. 14 No. 2 Mar. 1996.

Takeda et al, "Iodine imaging in thyroid by fluorescent X-ray CT with 0.05 mm spatial resolution", Nuclear Instruments and Methods in Physics Research A 467-468 (2001) 1318-1321.

Vekemans et al, "Processing of three-dimensional microscopic X-ray fluorescence data", JAAS, J . Anal. Al. Spectrom, 2004, 19, 1302-1308.

Woll et al, "Development of confocal X-ray fluorescence (XRF) microscopy at the Cornell high energy synchrotron source", Appl. Phys. A 83, 235-238 (2006).

Yu et al, "Preliminary experiment of fluorescent X-ray computed tomography to detect dual agents for biological study", Inlemalional Union of Crystallography, J. Synchrotron Rad. (2001), 8, 1030-1034.

Zamburlini et al, "In vivo study of an x-ray fluorescence system to detect bone strontium non-invasively", Phys. Med. Biol. 52 (2007) 2107-2122.

Xos, "Micro X-ray Fluorescence (uXRF)", http://www.xos.com/techniques/xrf/micro-x-ray-fluorescence-%CE%BCxrf/, downloaded, Jan. 5, 2011.

Ding, Xunliang et al., "X-ray spectrometry using polycapillary X-ray optics and position sensitive detector", www.elsevier.com:locate:talanta, Sep. 28, 1999.

* cited by examiner (a) Standard line-by-line scanning method (Mode 1)

(b) Slice-by-slice scanning method (Mode 2)

*Mode 2*

Synchrotron x-ray beam (c) Whole-volume irradiation method (Mode 3)

*Mode 3*

(d) Line-by-line scanning with multiple-slit apertures (LBL2) (Mode 4)

*Mode 4*

400

700

800

METHOD AND APPARATUS FOR MEASURING PROPERTIES OF A COMPOUND

PRIOR APPLICATION

The present application claims the benefit of priority to U.S. Provisional Application No. 61/293,118 filed on Jan. 7, 2010, which is hereby incorporated herein by reference.

STATEMENT AS TO FEDERALLY SPONSORED RESEARCH

This invention was made with government support under DE-AC02-06CH11357 awarded by Argonne National Laboratory and the Department of Energy. The government has certain rights in this invention.

FIELD OF THE DISCLOSURE

The present disclosure relates generally to a method and apparatus for measuring properties of a compound.

BACKGROUND

Fluorescence X-ray techniques are widely used for elemental analysis. It offers an excellent sensitivity to trace elements down to picogram level. With the use of synchrotron X-ray sources, 3-D mapping of trace elements inside volumetric samples can be obtained with the so-called fluorescence X-ray computed tomography (XFCT) techniques [1]-[10]. In most of XFCT studies, a pencil-beam of synchrotron X-rays are used to scan through a volumetric sample from multiple view-angles, as shown in FIG. 1.a. Fluorescence X-rays, originated from the subvolume excited by the beam, are collected by a nonposition-sensitive x-ray spectrometer. 3D distribution of trace elements can be reconstructed from the measured line-integrals. As an alternative imaging scheme, confocal geometry has also been explored by many authors.

Chukalina et al. have reported an analytical evaluation of XCFT with a converging aperture system [11]. Woll et al. [12] and Vekemans et al. [13] have reported the use of polycapillary x-ray optics for confocal fluorescence x-ray microscopy. Similar to the line-by-line scanning scheme, these methods rely on scanning the focal-spot point-by-point through the volume (or surface)-of-interest to obtain a spatial mapping of trace elements. Despite the excellent imaging performances demonstrated in these studies, the need for mechanical scanning leads to long imaging times. In recent years, many efforts have been dedicated to improve the speed of XFCT studies [6], [7]. This is important for potential in vivo imaging applications as those reported by Takeda et al. [8]-[10]. The improved data acquisition speed allows for a greater throughput for XFCT studies with a limited beam time, which could make XFCT a more practical imaging modality for a wide range of applications.

DETAILED DESCRIPTION

Figure 1A:
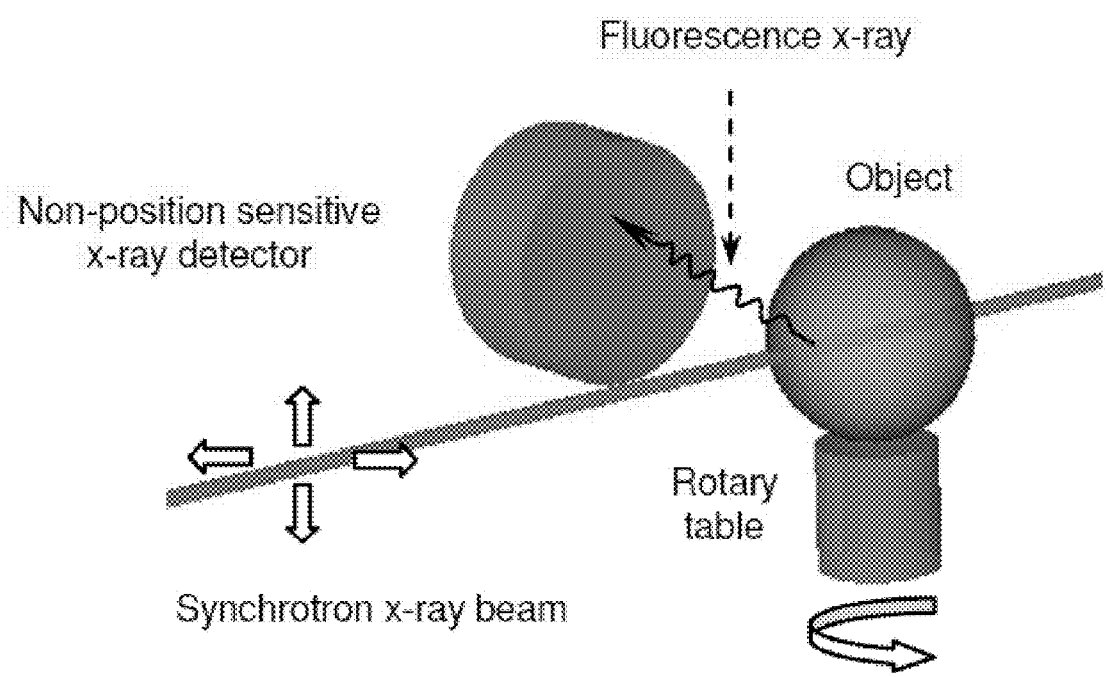
FIG. 1A depicts an illustrative embodiment of a prior art imaging approach for XFCT studies.

One embodiment of the present disclosure entails an apparatus having a collimator and a fluorescence detector. The collimator can be positioned next to a compound. The collimator can have at least one aperture. The aperture can be made of a thin sheet of heavy metal, such as gold and tungsten, with openings machined through the metal sheet. The compound emits fluorescence X-rays when impacted by an X-ray beam generated by an X-ray source. The collimator in turn can absorb at least a first portion of the fluorescence X-rays emitted by the compound and allow a second portion of the fluorescence X-rays to pass through the aperture to be detected by the fluorescence detector placed in proximity to the aperture. A three-dimensional (3-D) rendering of an elemental distribution of the compound can be determined from the fluorescence X-rays detected and the directional information.

One embodiment of the present disclosure entails a method for receiving fluorescence X-rays responsive to an X-ray beam impacting an object, wherein the fluorescence X-rays have known directional information, measuring energy from the fluorescence X-rays, and constructing a three-dimensional (3-D) rendering of an elemental distribution of the object according to the measured energy of the fluorescence X-rays and their corresponding directional information.

One embodiment of the present disclosure entails a computer-readable storage medium having computer instructions to measure energy from fluorescence X-rays emitted by a compound impacted by an X-ray beam, and to construct a three-dimensional rendering of an elemental distribution of the compound according to the measured energy of the fluorescence X-rays and their corresponding directional information.

The present disclosure presents a feasibility study for using detection systems similar to those commonly used in emission tomography (ET) for X-ray fluorescence computer tomography (XFCT). The present disclosure illustrates a detection system that combines high-resolution semiconductor detectors with apertures that are made of heavy metal sheets having arbitrary opening patterns. Possible opening patterns include, but not limited to pinhole, multiple-pinhole, coded-aperture, slit, or multiple-slit.

The key advantage of using an ET-based detection system is that 3-D distributions of trace elements can be built up with much reduced scanning time. In comparison to the conventional line-by-line scanning scheme, the ET-based imaging system allows a great reduction in imaging time, which has been one of the major hurdles for current XFCT studies. In order to compare different imaging schemes for XFCT studies, an analytical performance index was developed that is based on the fundamental tradeoffs between image noise and spatial resolution achievable with given detection configurations. To further demonstrate the feasibility of using SPECT apertures for XFCT, a prototype multiple-pinhole imaging system using a charge-coupled device (CCD) detector was setup at the Advanced Photon Source (APS) for imaging phantoms that contain solutions of several trace metals. Simultaneously acquired 3-D distributions of these elements are presented.

Figure 1B:
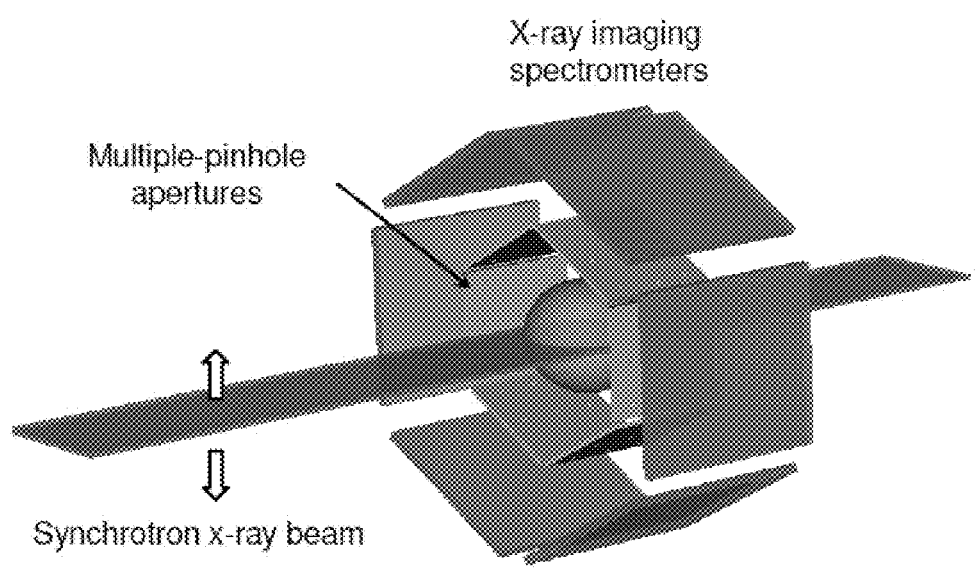
FIGS. 1B-1D depict illustrative embodiments of novel imaging approaches for XFCT studies.
Figure 1C:
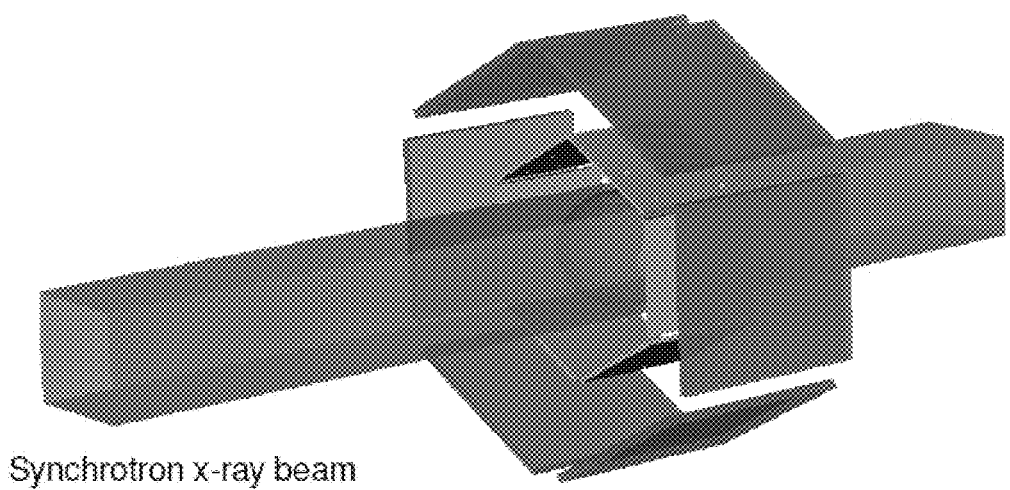
Figure 1D:
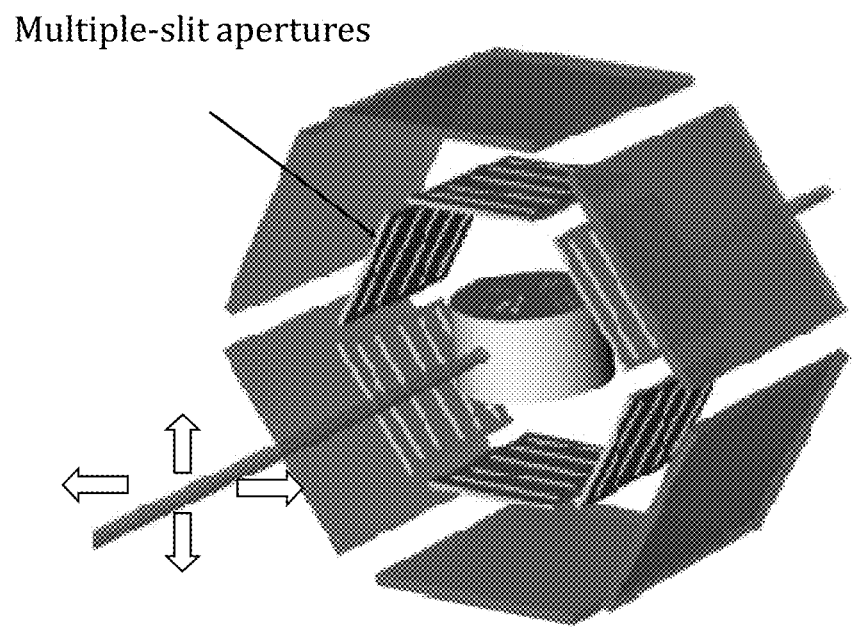

The present disclosure illustrates an imaging scheme for XFCT studies. With this scheme, the object is illuminated by a broad beam of synchrotron x-rays. Fluorescence photons are collected by a specialized emission tomography (ET) system that consists of multiple ultrahigh resolution x-ray imaging-spectrometers, coupled to several multiple-pinhole apertures. Two variations of this imaging scheme are shown in FIGS. 1B and 1C. Unlike in the line-by-line scanning approach, projections of the (fluorescence) x-ray-emitting object are acquired simultaneously from multiple view-angles. It is therefore possible to obtain a sufficient angular sampling using a much-reduced scanning motion, or even with a stationary setup. This approach offers the potential for a greatly improved imaging speed. In this research, Monte Carlo and experimental approaches were used to verify the feasibility of the ET-based approach for XFCT. The results are presented below.

In typical XFCT studies, the sample is scanned line-by-line with a pencil-beam of synchrotron x-rays. Fluorescence photons emitted from the narrow strip of volume illuminated by the beam are collected using a none-position-sensitive x-ray spectrometer. The number of fluorescence photons detected at a given beam position provides a line-integral of x-ray emission from the thin stripe. Volumetric distribution of trace elements can be reconstructed with either filtered backprojection (FBP) or (penalized) maximum-likelihood (ML) algorithms previously developed for various nuclear imaging modalities. The image formation process is very similar to those for both single-photon emission computed tomography (SPECT) with parallel-hole collimators and x-ray CT imaging with the first generation geometry. The attenuations of both synchrotron x-rays and fluorescence x-rays can be estimated based on the transmission CT images acquired simultaneously with a second detector operated in the standard x-ray CT mode, as previously discussed in [6][7].

The present disclosure proposes an alternative imaging scheme for XFCT studies. Instead of using a pencil-beam of synchrotron x-rays, the object is illuminated with two beam configurations as shown in FIGS. 1B and 1C. With these approaches, the object is either scanned by a thin slice or irradiated with a fixed broad beam of synchrotron x-rays. In either cases, fluorescence x-rays emitted from the object are collected by a detection system that consists of multiple x-ray imaging-spectrometers coupled to multiple-pinhole apertures. The detection system is very similar to that used for single photon emission computed tomography (SPECT), except that a very high energy-resolution is required to distinguish fluorescence x-rays emitted by different trace metals and to separate fluorescence photons from Compton scattered x-rays. 3-D distribution of trace-metals can be reconstructed from the projection data acquired with the ET-based detection system.

In comparison to the line-by-line scanning scheme, the proposed ET-based sampling method offers several attractive aspects. Firstly, with Mode 2 and 3 geometries (shown in FIG. 1), the much-simplified scanning motions would potentially lead to a much-reduced imaging time. Secondly, with the line-by-line scanning, the angular sampling achieved is limited by (a) the mechanical scanning procedures that can be practically implemented and (b) the constraints on imaging time and dose delivery during the measurement. In contrast, the multiple-pinhole based detection system provides projections simultaneously from many view angles. This can potentially be translated into an improved image quality. Thirdly, with carefully designed Mode 2 geometries, it is possible to remove the multiplexing in projection data. Therefore, the origin of each detected x-ray is confined to a distinct voxel (or a small group of voxels) in the object. In comparison to the use of Mode 1 and Mode 3 geometries, the nonmultiplexing projections acquired with Mode 2 leads to reconstructed images that are free of spatial correlation of imaging noise, as typically seen in reconstructions with multiplexed data. This could offer a superior image quality for objects that have extended distribution of trace-elements.

There are three major concerns for the ET-based XFCT approach. Firstly, high-resolution SPECT detection systems typically require the use of collimation apertures that have very small open-fractions ($10^{-3}$-$10^{-2}$). Compared to the line-by-line scanning geometry, the ET-based approach uses a wider x-ray beam to illuminate a greater portion of the object, which leads to a much stronger fluorescence signal from the object. This partially compensates for the low detection efficiency. Therefore, the key uncertainty is whether the use of ET-based can provide an improved signal-to-noise ratio with comparable imaging times. Secondly, Mode 2 and 3 tend to deliver a greater amount of radiation dose per unit imaging time. Although radiation doses may not be a serious issue for nonbiological samples, it does pose limitations for potential in vivo studies [9][10].

Considering the reduced imaging time with Mode 2 and 3, it is important to quantify how much radiation dose will be delivered per imaging study. Thirdly, the spatial resolution provided by Mode 2 and 3 geometries is limited by the size of the pinholes. Given the constraints on aperture fabrication and the considerations on detection efficiency, the use of pinholes of less than 25 μm diameter is less practical. Therefore, the spatial resolution offered by the ET-based detection system is typically limited to several tens of microns to a few hundred microns. In comparison, the line-by-line scanning scheme allows for a spatial resolution at submicron level, although this would require a long imaging time.

The concerns on radiation dose and imaging time may be mitigated by the use of a synthetic imaging strategy. During an imaging study, the entire object is first imaged with Mode 3 for a short period. This provides a quick snapshot with a relatively low radiation dose. The image obtained helps to define regions-of-interest (ROI) in the object. Once the ROIs are defined, the beam profile is then modified to illuminate the selected sub-volumes only with a thin slice of synchrotron x-rays (Mode 2). This provides high quality images of the ROIs with a fast imaging time and a limited radiation dose delivered to a fraction of the sample volume only.

For quantitative comparisons between different imaging modes, GEANT 4 [14] was used to model x-ray interactions and an analytical package (developed in our previous studies [15]-[18]) to model the response of the detection system for fluorescence x-rays emitted from the sample. For a given object illumination scheme (line-by-line, slice-by-slice or whole volume illumination), the system response function (SRF) is typically represented by a matrix. Each of its elements gives the average number of fluorescence photons that are originated from a given source voxel containing a unit concentration of trace-element and detected on a given detector element. In this study, most of interaction physics was incorporated, such as photoelectric effect, Compton scattering, Rayleigh scattering in the system model. The X-ray fluorescence process was modeled using the low-energy physics (LEP) package (as part of GEANT4) that was specially developed for the transport of low energy electromagnetic radiation through matter. Polarization of synchrotron x-rays was included in the study to account for the non-isotropic distribution of Compton background.

To evaluate the line-by-line scanning approach (Mode 1 in FIG. 1), two similar imaging configurations were included. The first one uses a square beam of 100 µm×100 µm cross section to scan through the object from 180 view angles, with an angular step size of 2 degrees. At each angular position, the beam steps through the object in 64×64 equally spaced steps. The second configuration uses 200 µm beam-width and 32×32 linear steps at each view angle. Fluorescence x-rays are collected by a nonposition-sensitive spectrometer that has a fixed detection efficiency of 20% for x-rays of 27-32 keV emitted from any location in the object. The detector has an energy resolution of 250 eV that was modeled with Gaussian functions.

The ET-based detection system consists of a ring of six detectors. The opposite detectors are positioned 2.4 cm apart. The simplified x-ray detector consists of 256×256 square pixels of 55 µm×55 µm in size. The detector has a detection efficiency of 100% at 30 keV and an energy resolution of 1.5 keV modeled with a Gaussian functions. The depth-of-interaction effect was not modeled in the simulation. All events detected were assumed to be full-energy event. A multiple pinhole aperture is placed in front of each detector. The aperture was made of pure gold of 250 µm thickness. Both the aperture-to-object-center distance and the aperture-to-detector distance were 6 mm. In this study, we examined two aperture configurations with 6×6 and 11×11 pinholes respectively. The distances between adjacent pinholes are 1.5 mm and 0.8 mm for the two patterns. Note that the actual pinhole locations are randomly shifted by an average of 0.1 mm from the designated grid points in the square patterns. The pinhole diameter is 100 µm with sharp knife-edge and acceptance cones of 45 degrees on both sides.

The object simulated is a cylinder of 6.4 mm diameter and 6.4 mm long. It is filled with a uniform water solution of I-127 with a concentration of 0.1 mg/g. Six groups of hot rods were also inserted for comparing the imaging resolution achieved in reconstruction. The diameters of hot-rods in each group are 1.25 mm, 1 mm, 0.75 mm, 0.5 mm, 0.3 mm and 0.2 mm respectively. Within each group, the minimum spacing between centers of two adjacent holes is two times their diameter. In this study, monochromatic x-rays of 35 keV were used to irradiate the object and the x-ray beam has a fixed intensity of $10^6$ per second per mm$^2$. Fluorescence x-rays of around 27 keV were selected with an energy window of 2 keV in width.

To compare the imaging performances offered by different XFCT imaging schemes, we used the modified Cramer-Rao bound (MUCRB) as an analytical performance index [19] [20]. This approach is based on a simple idea. In many cases, the user may have some ideas on the spatial resolution functions that are required to fulfill an imaging task. Therefore, a "good" imaging system could be chosen as the one that delivers a resolution function similar to the target resolution function, whilst having the lowest possible variance on a given pixel or the lowest average variance across an arbitrarily selected cluster of pixels in the image. This method is briefly described below.

For laying out the basic imaging problem, let's use $x=[x_1, x_2, \ldots, x_N]^T \in R^N$ to denote the set of unknown parameters, e.g., the concentrations of a given trace-element across all the voxels in the object. The mapping from x to the projection data y is governed by a conditional probability density function p(y;x). For XFCT studies, y is a collection of random Poisson (or Gaussian) variables that represent the measured numbers of fluorescence x-rays detected on each detector element. The expectation of y is given by the following transform $$\bar{y} = A \cdot x + r, \qquad (1)$$

where A is the system-response matrix as described in Section II.D. r denotes extra noise components. $\hat{x}=[\hat{x}_1, \hat{x}_2, \ldots, \hat{x}_p]^T$ is an estimator of the underlying distribution of a trace metal in the sample, whose mean is $$\mu(\hat{x}) = E_x[\hat{x}(y)] = \int \hat{x}(y) \cdot p(y;x) \cdot dy, \qquad (2)$$

where E[•] denotes the expectation operator.

The subsequent question is how to put a constraint on the spatial resolution function delivered by a given imaging strategy? For an imaging system, the spatial resolution function is typically represented by the linearized local-impulse function (LIR) [21]. For the j'th voxel, it is defined as $$l_j(x) = \lim_{\delta \to 0} \frac{\mu(x + \delta e_j) - \mu(x)}{\delta} \qquad (3)$$

$$= [\partial E(\hat{x}_1)/\partial x_j, \partial E(\hat{x}_2)/\partial x_j, \ldots, \partial E(\hat{x}_N)/\partial x_j]^T.$$

To provide closed form solutions for system comparison or optimization, one can substitute LIR with the mean gradient vector, defined as $$g_j = \nabla_x E(\hat{x}_j) \qquad (4)$$

$$= [\partial E(\hat{x}_j)/\partial x_1, \partial E(\hat{x}_j)/\partial x_2, \ldots, \partial E(\hat{x}_j)/\partial x_N]^T.$$

It is easily shown that $l_j$ and $g_j$ defined in (3) and (4) are closely related. They become identical if the mean gradient matrix is symmetric. Suppose that we know a priori the desired point-spread function (or the mean gradient vector) at the j'th voxel is $f_j$, we can define a similarity measure $$\|g_j-f_j\|_C \leq \gamma, \quad (5)$$

where $\gamma$ is a threshold that governs the degree of similarity between $f_j$ and $g_j$. $C$ is a symmetric and positive definite weighting matrix. $\|.\|$ is the Euclidean norm of a vector, so that $$\|g_j-f_j\|_C^2 = (g_j-f_j)^T \cdot C \cdot (g_j-f_j). \quad (6)$$

All estimators that satisfy constraint (5) with a small $\gamma$ would offer spatial resolution functions similar to the target f, regardless the physical system configuration and the estimation method used.

It has been previously shown that for an imaging system/strategy to deliver a spatial resolution satisfying (5), the minimum variance attainable at a given pixel is bounded by [19], [20]

$$\mathrm{Var}(\hat{x}_j) \geq f_j^T \cdot [J + (\lambda \cdot C)^{-1}]^{-1} \cdot J \cdot [J + (\lambda \cdot C)^{-1}]^{-1} \cdot f_j, \quad (7)$$

where $\lambda$ is a scalar constant. The mean-gradient vector of the efficient estimator that achieves this bound is given by $$g_{optimum} = J \cdot [J + (\lambda \cdot C)^{-1}]^{-1} \cdot f_j, \quad (8)$$

where J is the Fisher information matrix (FIM) that is defined as $$J = E\left\{ \left[ \frac{\partial \log p(y;x)}{\partial x} \right] \cdot \left[ \frac{\partial \log p(y;x)}{\partial x} \right]^T \right\}. \quad (9)$$

Note that the efficient estimator that (asymptotically). In this study, we used (7) and (8) to evaluate the full-width-at-half-maximum (FWHM) of the point-spread-function and the minimum variance attainable at a given point j in the reconstructed image. By varying the target resolution function $f$, one can obtain a curve representing the tradeoffs between imaging resolution and pixel-wise variance. It was used as the basis for comparing the different imaging schemes for XFCT studies.

Figure 2:
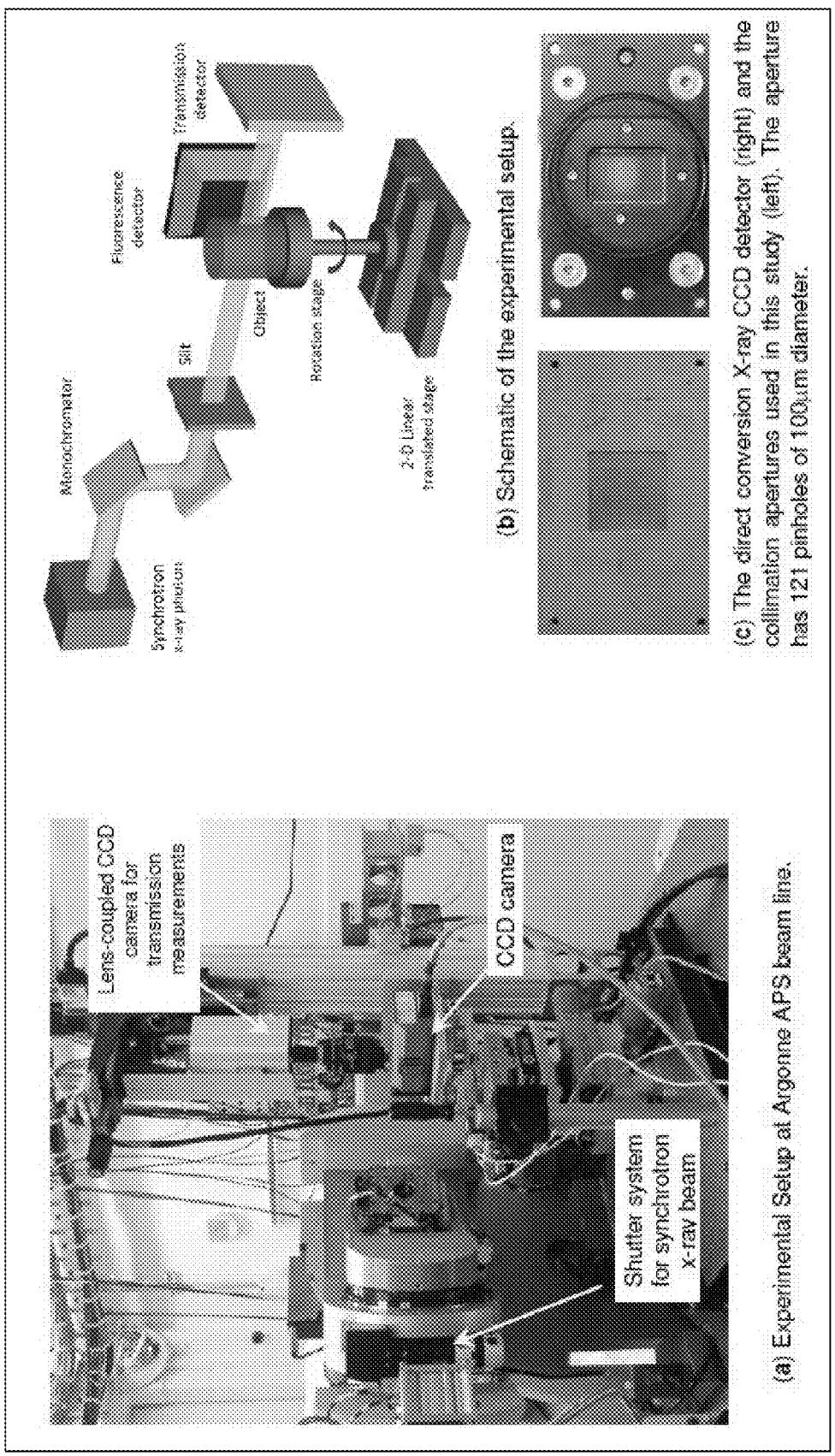
FIG. 2 depicts an illustrative embodiment of the experimental setup for the preliminary XFCT study. The detection system consists of an X-ray CCD detector, a multiple pinhole aperture.

The experimental setup used in this feasibility study is shown in FIG. 2. The ET-based detection system consists of a single front-illuminated X-ray CCD detector produced by Andor Technology (Model #934N). It has a detection area of 2.56 cm×1.52 cm, with 1280×768 square pixels of 20 μm×20 μm in size. The detection efficiency of the detector is ~80% at 5 keV, ~30% at 10 keV and ~15% at 15 keV. The space around the CCD sensor was filled with dry hydrogen and the sensor was cooled to −15° C. to reduce dark noise. X-ray interactions were identified with a photon-counting algorithm that was previously described in [16], [22]. This process offers an energy resolution of ~250 keV FWHM. To "simulate" the data acquisition process in Mode 3, the object is rotated with 32 angular steps during a study as shown in FIG. 2B.

In this study, synchrotron x-rays of 15 keV were used to irradiate the sample. The beam profile was modulated with a PC controlled aperture that can provide both thin parallel beams (down to a few μm in width) and extended beam with a maximum cross section of 5 mm×5 mm. The beam intensity was fixed at ~$10^9$ photons per second per mm². An x-ray shutter was installed on the beam line, whose operation was synchronized with the readout of the CCD to eliminate the smearing effect. In this study, the CCD was typically operated with 1-5 second accumulation time followed by a readout period of 1 s.

Two multiple-pinhole apertures were tested with the CCD detector. The first one has 3×5 pinholes of 300 μm diameter and a pinhole distance of 3 mm. The second aperture has 35 pinholes of 100 μm diameter, arranged in a 5×7 array with 1.6 mm spacing between adjacent pinholes. Both apertures were fabricated with tungsten sheets of 500 μm thickness. The pinholes have cone-shaped profiles on both sides, with a fixed acceptance-angle of 45 degrees. The detector-to-aperture distance was 1.5 mm and the center of the object is 1.2 mm from the aperture. The phantom used in this experimental study consists of three plastic tubes of 0.75 mm inner diameter. These tubes were filled with uniform solutions containing 0.1 μMole Fe, Zn and Br respectively. A larger plastic tube was used to hold the three tubes together. Its inner diameter is around 1.6 mm.

Figure 3:
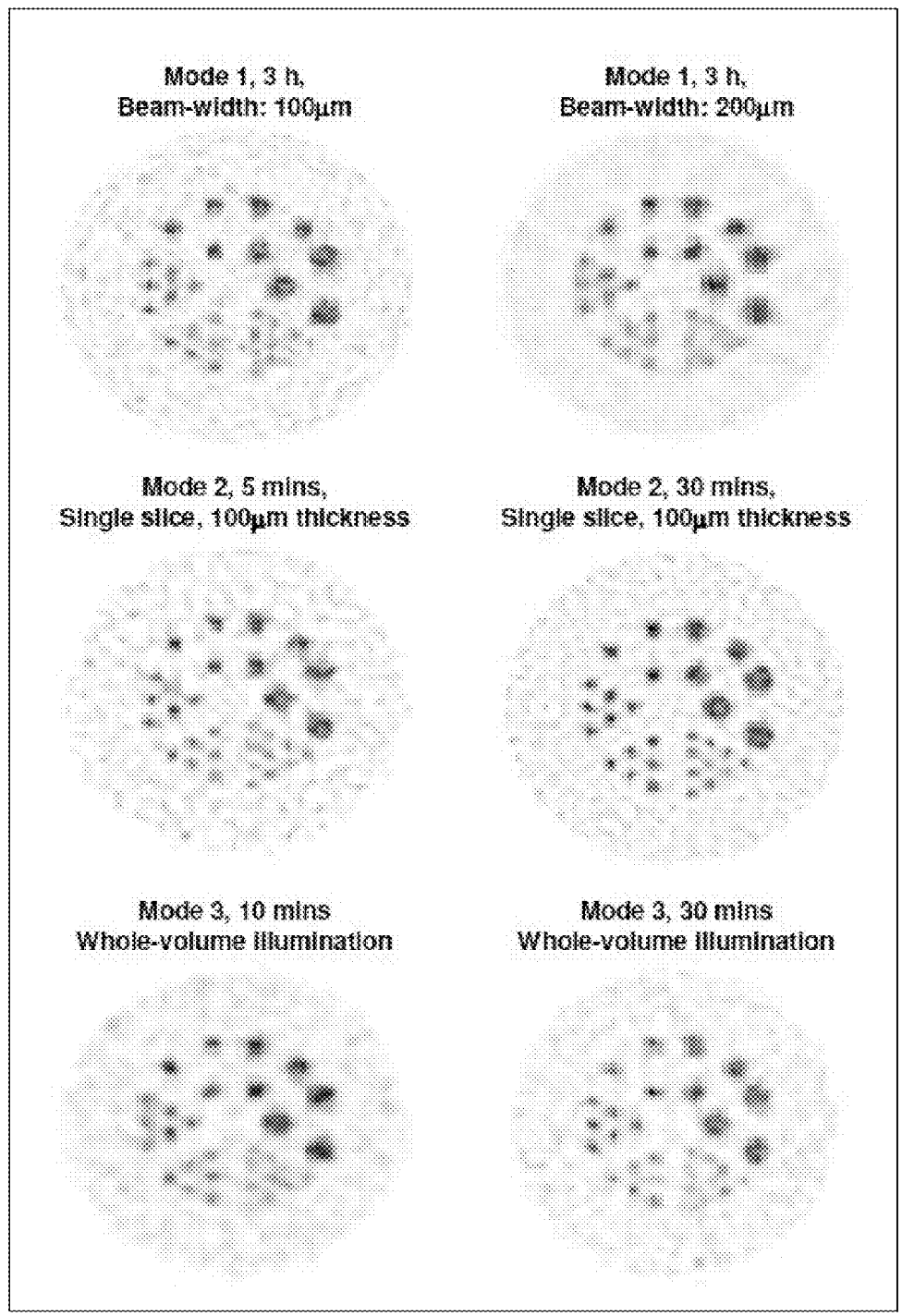
FIG. 3 depicts an illustrative embodiment of reconstructed phantom images. The imaging mode, data acquisition time and beam configurations are shown above each figure. Images were chosen to have the same variance at the center. The 36 pinhole apertures were used for the ET-based detection system.

The performance benefit of ET-based XFCT approach over the conventional line-by-line scanning approach is demonstrated in FIG. 3. These images were chosen to have similar variances at the center. In this study, the 36 pinhole aperture (216 pinholes with the entire system) was used with the ET-based detection system. This configuration offers a detection efficiency of 0.16% for fluorescence x-rays emitted from the center of the object, which is a factor of 100 lower than that for the detection system simulated in Mode 1 (20%). Despite the low detection efficiency, both Mode 2 and 3 have delivered similar or better images with much reduced imaging times. As previously discussed, using Mode 2 with carefully selected geometries (e.g. the detectors being very close to the apertures), it is possible to eliminate the multiplexing in projections. This leads to a superior imaging quality, with a much-suppressed spatial correlation of image noise across the FOV.

Figure 4:
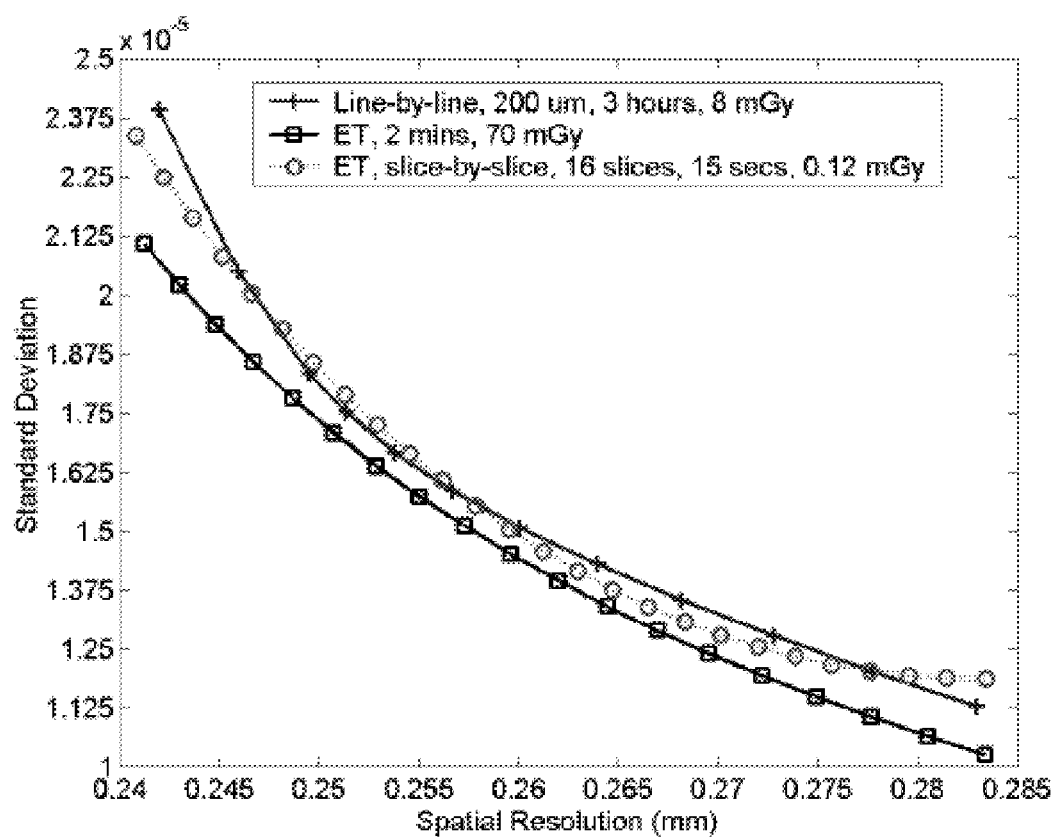
FIG. 4. depicts an illustrative embodiment of the comparison between the resolution-variance tradeoff curves achieved with the ET-based approach and the line-by-line scanning approach. The curves are chosen to be reasonably close to each other, indicating similar imaging performances achieved with different approaches. The great reduction in imaging time with the ET-based approach is demonstrated.

For quantitative comparison, the resolution-variance tradeoff curves achieved were plotted with the three data acquisition modes as shown in FIG. 4. In this case, the ET-based detection system had a total of 726 pinholes (11×11 pinholes per detector head), which provides a detection efficiency of 0.8% for x-rays emitted from the center of the object. When compared to the line-by-line approach, the ET-based detection system allows one to reduce the imaging time by almost two orders of magnitude. The radiation dose delivered to the object was evaluated with GEANT 4 simulations and shown in FIG. 4. It is not surprising that the use of a broad beam in Mode 3 leads to a substantially increased radiation dose. For example, a 2-minute study with the Mode 3 delivers 70 mGy dose to the object. It is almost 10 times of the dose (8 mGy) delivered by a line-by-line study that lasts 180 minutes.

As previously discussed in Sec. II.D, both radiation dose and imaging time can be reduced by the use of a synthetic imaging strategy. If the final imaging task is to map the distribution of a trace element within a sub-volume only, one can start from a quick scan using Mode 3, followed by a slice-by-slice scan in Mode 2 through the volume-of-interest only. When compared to the conventional line-by-line scanning approach, the synthetic imaging approach would allow high-speed XFCT studies with a superior image quality and a much reduced radiation dose. This is evident in the comparison shown in FIG. 4.

Figure 5:
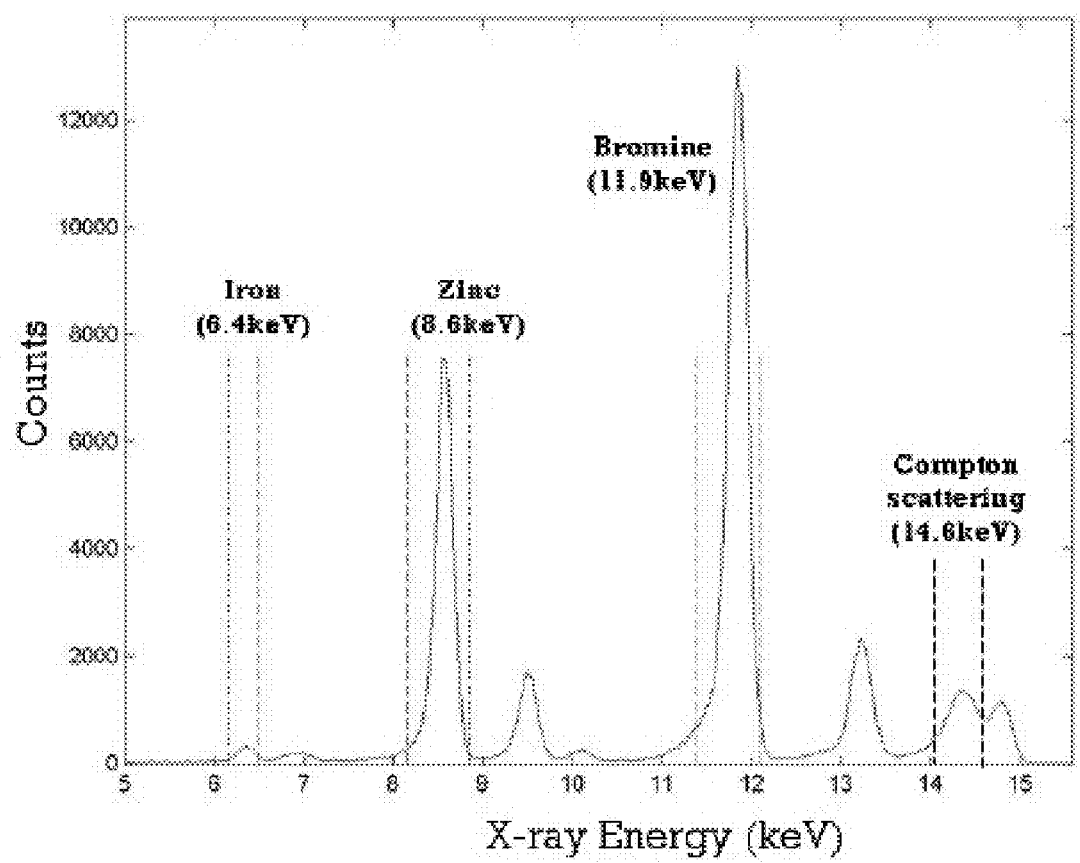
FIG. 5. depicts an illustrative embodiment of the energy spectrum measured with the X-ray CCD detector. The energy threshold used for selecting fluorescence components are shown in the figure.
Figure 6:
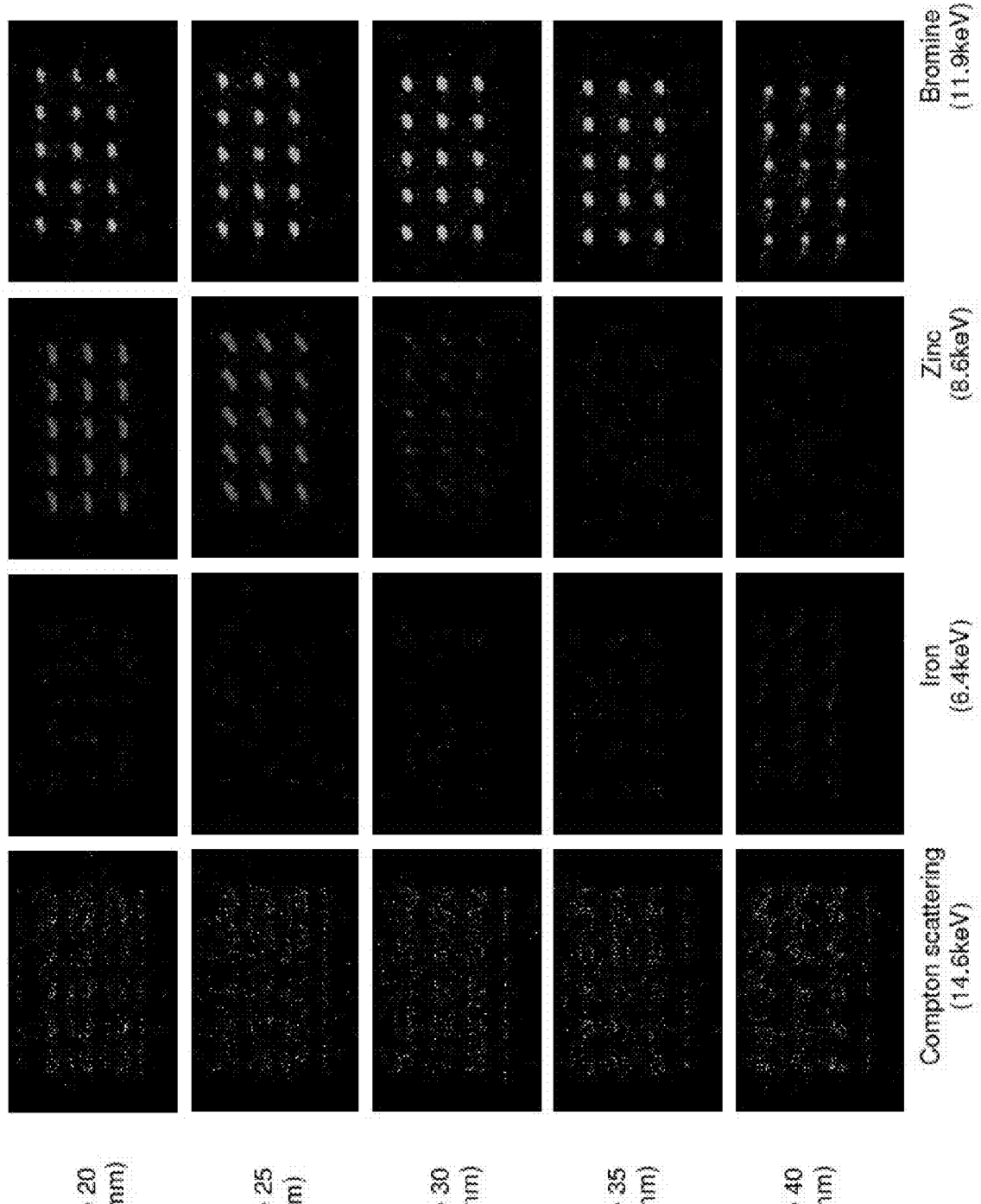
FIG. 6. depicts an illustrative embodiment of the experimentally acquired projections with fluorescence and Compton scattered x-rays. The aperture used has 35 pinholes of 300 µm diameter. The projection data was acquired by stepping a thin x-ray beam of 50 µm thickness through the object. Data acquisition time was 5 minutes per slice.
Figure 7:
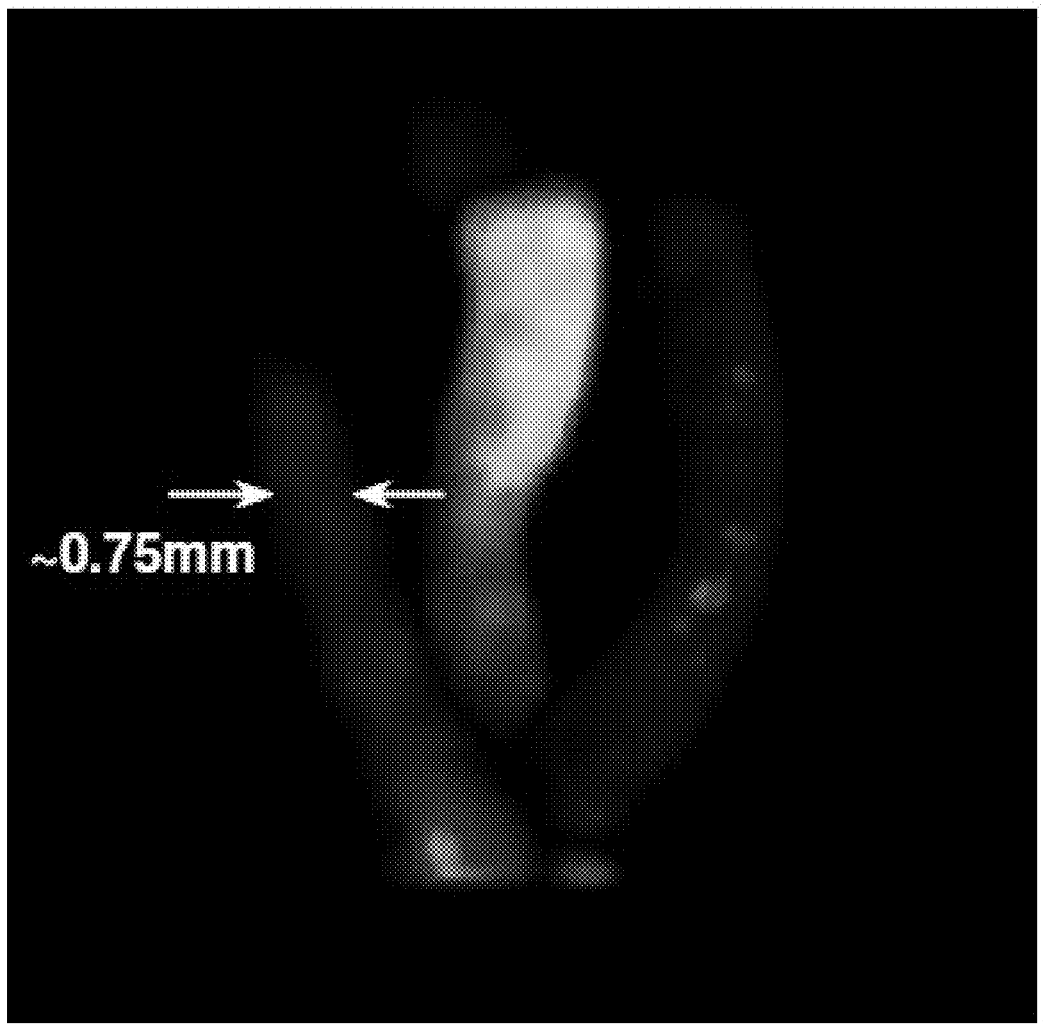
FIG. 7. depicts a 3-D rendering of the reconstructed elemental distribution with data acquired in Mode 2 geometry.

An energy spectrum measured with the CCD sensor is shown in FIG. 5. The FWHM value around the Br photopeak was around 250 eV, which allows us to resolve most of x-ray lines from the three trace elements. In the first measurement, we used Mode 2 geometry and step the slice-beam in 50 μm through the object. The projections acquired with the CCD detector coupled to the 15 pinhole aperture is shown in FIG. 6. The distribution of Fe, Zn and Br inside individual slices illuminated by the beam were reconstructed with the standard MLEM algorithm. A 3-D volumetric distribution can be built up by stacking the reconstructed slices together as shown in FIG. 7.

Figure 8:
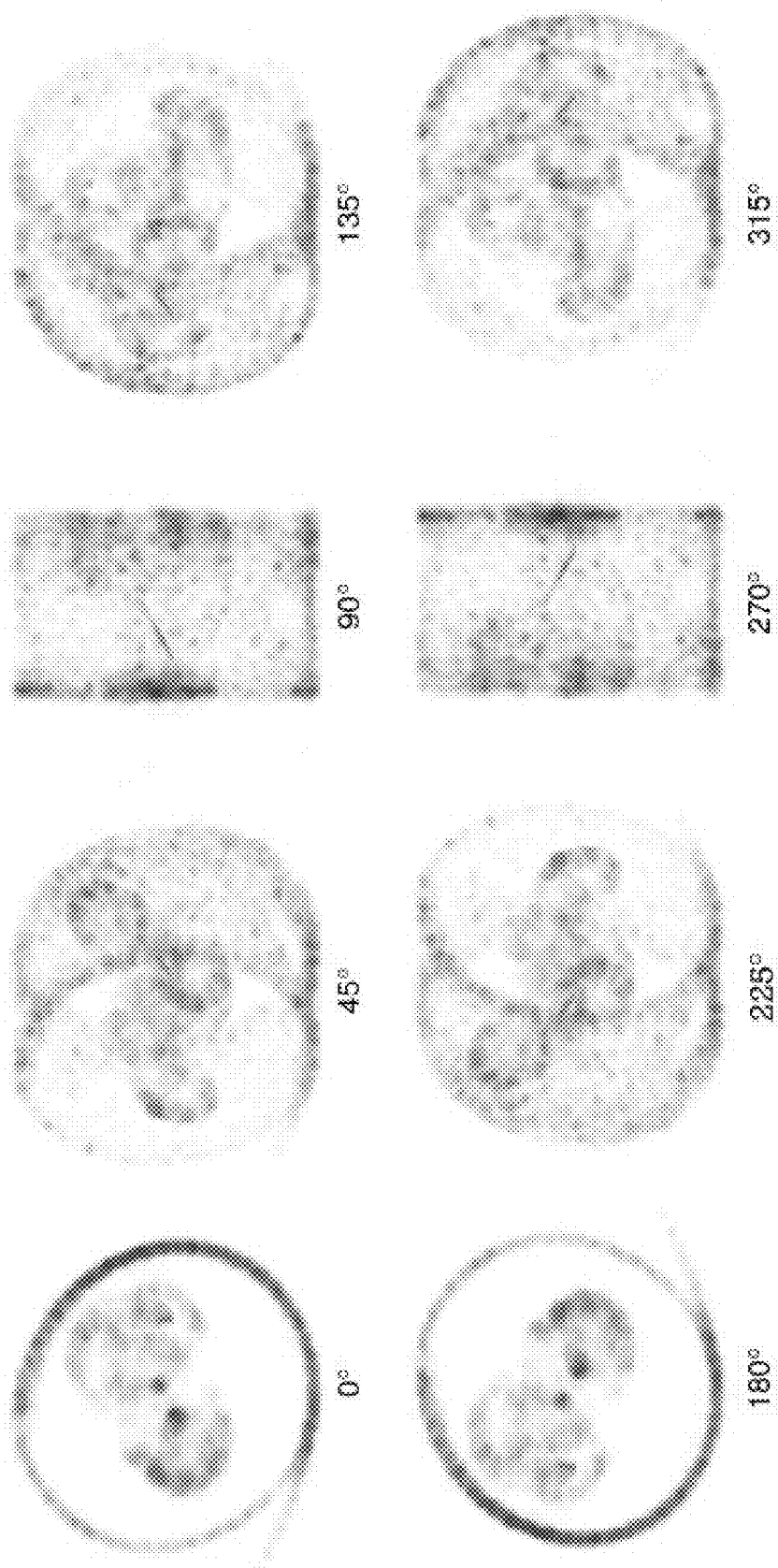
FIG. 8. depicts a 3-D rendering of the reconstructed Bromine (green) distribution superimposed on the electron density measured based on Compton scattered x-rays (gray scale)

In the second measurement, the object is exposed to a broad beam of synchrotron x-rays that was suppose to cover the entire object. The object was rotated with 32 angles during the measurement, which takes around 3 hours to complete. Unfortunately, the beam was mistakenly aimed too high and missed the section containing most of the solutions. Therefore, we were only able to resolve the Br peak and the Compton components in the spectrum acquired. Using the projections with Br and Compton scattered x-rays, 3-D images were reconstructed and shown in FIG. 8. Interestingly, with Compton scattered x-rays, we were able to reconstructed the plastic tube structure, with some remnant Br distribution seen inside one of the tubes.

In the present disclosure, the use of ET-based detection system for XFCT studies were proposed and evaluated. Compared to the conventional line-by-line scanning approach, the ET-based approaches allow for tomographic imaging with a much-simplified scanning motion and (potentially) offer a more complete angular sampling. In this study, Monte Carlo simulations were used to compare the proposed approach with the conventional line-by-line scanning approach. The feasibility of ET-based approach for XFCT was also demonstrated with a prototype imaging system installed at the GSE-CARS beam line at the Advanced Photon Source (APS). Tomographic images were obtained based on both fluorescence and Compton scatter x-rays.

Despite the relatively low detection efficiency, the use of the ET-based system provides a substantially improved imaging speed (by 1 or 2 orders of magnitude) over that offered by the conventional line-by-line scanning approach. This would greatly improve the throughput with limited synchrotron beam time and therefore make XFCT a more practical imaging modality for a wide range of applications. For dose-sensitive studies, one can use the synthetic imaging strategy that combines XFCT studies with different sampling geometry, tailored for the given object. This could lead to XFCT studies with a fast data acquisition time, a relatively low radiation dose to the object and an excellent imaging quality.

Figure 9:
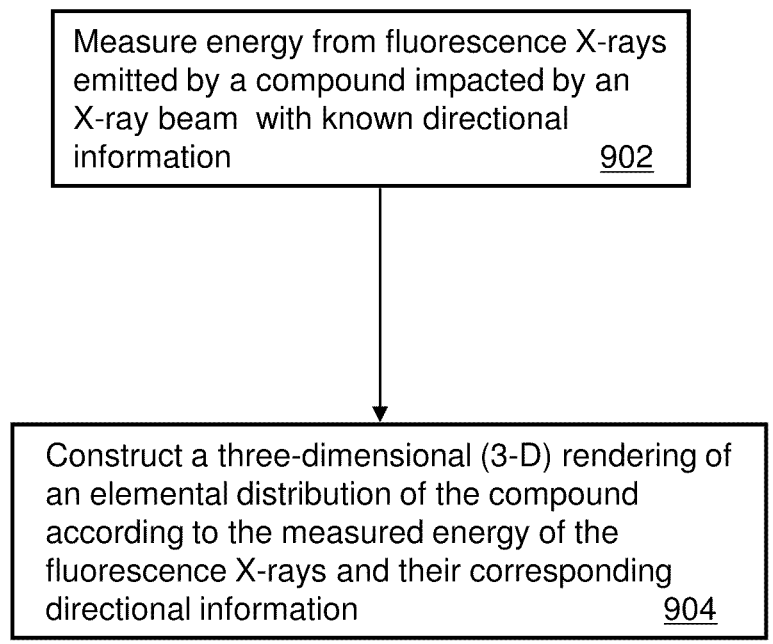
FIG. 9 depicts an illustrative method according to the present disclosure.

The illustrative embodiments above can be implemented in part by a computing system such as a computer, lap top, server, or mainframe computer according to method 900 of FIG. 9. At step 902, a computing system can measure energy from data supplied by a plurality of fluorescent detectors that detect fluorescent X-rays emitted by a compound impacted by an X-ray beam. The fluorescent X-rays have a known directional information based on the position of the collimators, the apertures, and the fluorescent detectors. At step 904, the computing system can construct a three-dimensional rendering of an elemental distribution of the compound determined from the measured energy of the fluorescence X-rays and their corresponding directional information.

Figure 10:
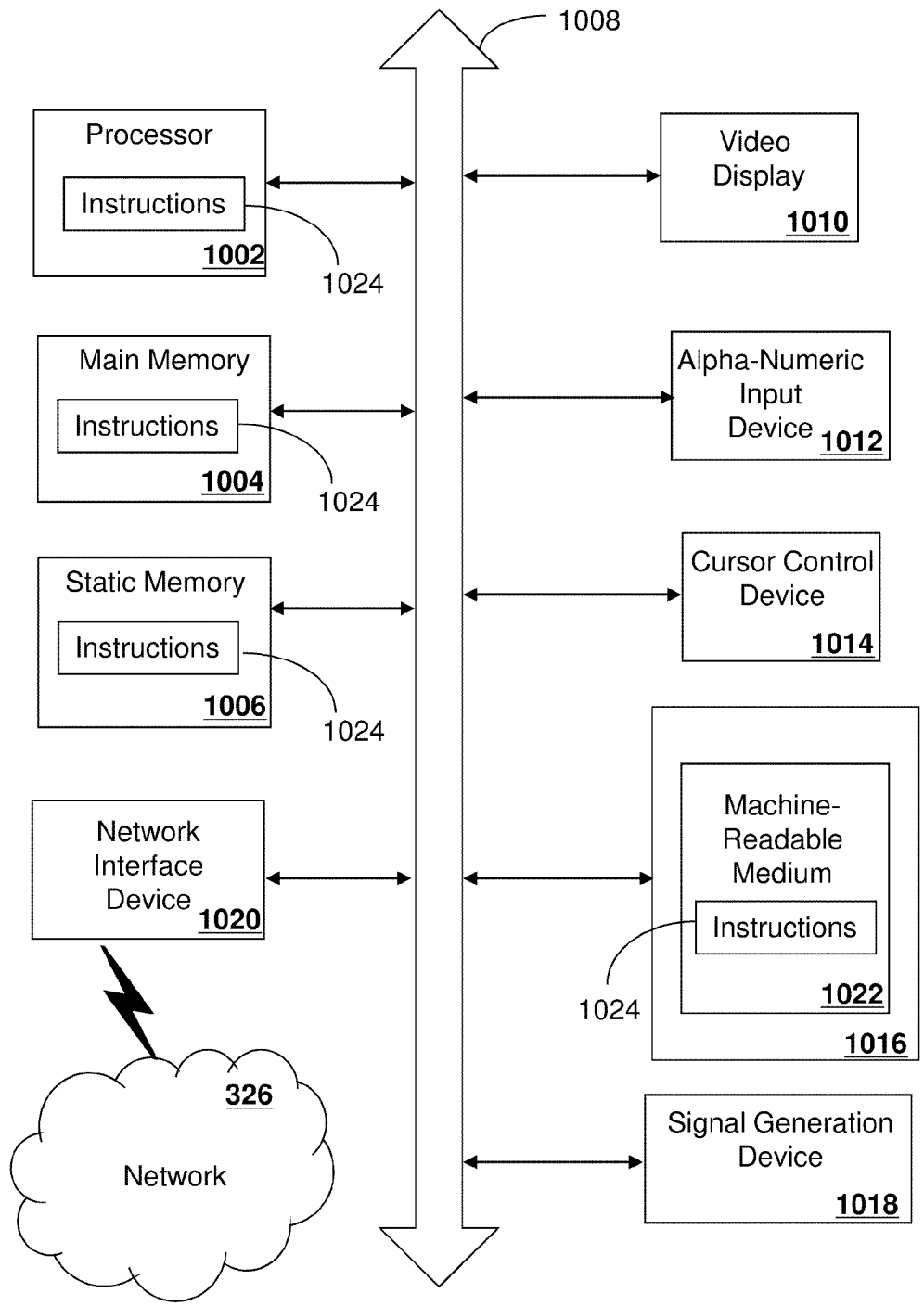
FIG. 10 depicts an illustrative diagrammatic representation of a machine in the form of a computer system within which a set of instructions, when executed, may cause the machine to perform any one or more of the methodologies disclosed herein.

FIG. 10 depicts an exemplary diagrammatic representation of a machine in the form of a computer system 1000 within which a set of instructions, when executed, may cause the machine to perform any one or more of the methods discussed above. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1000 may include a processor 1002 (e.g., a central processing unit (CPU), a graphics processing unit (GPU, or both), a main memory 1004 and a static memory 1006, which communicate with each other via a bus 1008. The computer system 1000 may further include a video display unit 1010 (e.g., a liquid crystal display (LCD), a flat panel, or a solid state display. The computer system 1000 may include an input device 1012 (e.g., a keyboard), a cursor control device 1014 (e.g., a mouse), a disk drive unit 1016, a signal generation device 1018 (e.g., a speaker or remote control) and a network interface device 1020.

The disk drive unit 1016 may include a tangible computer-readable storage medium 1022 on which is stored one or more sets of instructions (e.g., software 1024) embodying any one or more of the methods or functions described herein, including those methods illustrated above. The instructions 1024 may also reside, completely or at least partially, within the main memory 1004, the static memory 1006, and/or within the processor 1002 during execution thereof by the computer system 1000. The main memory 1004 and the processor 1002 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 622 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the present disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 1000.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. For example, FIG. 1D can provide a fourth mode in which collimators can have multiple slit apertures. Accordingly, combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

REFERENCES

[1] Q. W. Yu, T. Takeda, T. Yuasa, Y. Hasegawa, J. Wu, Thet-Thet-Lwin, K. Hyodo, F. A. Dilmanian, Y. Itai, and T. Akatsuka, "Preliminary experiment of fluorescent X-ray computed tomography to detect dual agents for biological study," *J. of Synchrotron Radiation*, vol. 8, pp. 1030-1034, 2001.

[2] M. Chukalina, A. Simionovici, L. Lemelle, C. Rau, L. Vincze, and P. Gillet, "X-ray fluorescence tomography for non-destructive semi-quantitative study of microobjects," *J. De Physique Iv*, vol. 104, pp. 627-630, 2003.

[3] M. Zamburlini, A. Pejovic-Milic, D. R. Chettle, C. E. Webber, and J. Gyorffy, "In vivo study of an x-ray fluorescence system to detect bone strontium non-invasively," *Physics in Medicine and Biology*, vol. 52, pp. 2107-2122, 2007.

[4] G. R. Pereira, M. J. Anjos, H. S. Rocha, P. Faria, C. A. Perez, and R. T. Lopes, "Computed tomography and X-ray fluorescence CT of biological samples," *Nucl. Instrum. Methods.*, vol. A580, pp. 951-954, 2007.

[5] M. Hansson, G. Berg, and M. Isaksson, "In vivo x-ray fluorescence analysis (XRF) of the thyroid iodine content—Influence of measurement geometries on the iodine K alpha signal," *X-Ray Spectrometry*, vol. 37, pp. 37-41, 2008.

[6] P. J. La Riviere, P. Vargas, M. Newville, and S. R. Sutton, "Reduced-scan schemes for x-ray fluorescence computed tomography," *IEEE Trans on Nucl. Sci*, vol. 54, pp. 1535-1542, 2007.

[7] Y. Hasegawa, Q. Yu, D. Noto, T. Takeda, K. Hyodo, T. Yasgiro, T. Yuasa, Y. Hiranaka, Y. Itai, and T. Akatsuka, "Improvement of Imaging Speed in Fluorescent X-Ray Computed Tomography Using Synchrotron Radiation," *IEICE Trans. on Information and Systems, Pt. 2 (Japanese Edition)*, Vol. J83-D-2, pp. 1539-1547, 2002.

[8] T. Takeda, et. al, "Fluorescent scanning x-ray tomographic image with monochromatic synchrotron x-ray," *Med. Imaging Technol.*, vol. 14, no. 2, pp. 183-194, March 1996.

[9] T. Takeda, Q. Yu, T. Yashiro, T. Zeniya, J. Wu, Y. Hasegawa, Thet-Thet-Lwin, K. Hyodo, T. Yuasa, F. A. Dilmanian, T. Akatsuka, and Y. Itai, "Iodine imaging in thyroid by fluorescent X-ray CT with 0.05 mm spatial resolution," *Nucl. Instrum. Methods*, vol. A467, pp. 1318-1321, 2001.

[10] T. Takeda, "Phase-contrast and fluorescent X-ray imaging for biomedical researches," *Nucl. Instrum. Methods*, vol. A548, pp. 38-46, 2004.

[11] M. Chukalina, A. Simionovici, S. Zaitsev, and C. J. Vanegas, "Quantitative comparison of X-ray fluorescence microtomography setups: Standard and confocal collimator apparatus," *Spectrochimica Acta Part B-Atomic Spectroscopy*, vol. 62, pp. 544-548, 2007.

[12] A. R. Woll, J. Mass, C. Bisulca, R. Huang, D. H. Bilderback, S. Gruner, and N. Gao, "Development of confocal X-ray fluorescence (XRF) microscopy at the Cornell high energy synchrotron source," *Applied Physics a-Materials Science & Processing*, vol. 83, pp. 235-238, 2006.

[13] B. Vekemans, L. Vincze, F. E. Brenker, and F. Adams, "Processing of three-dimensional microscopic X-ray fluorescence data," *Journal of Analytical Atomic Spectrometry*, vol. 19, pp. 1302-1308, 2004.

[14] http://www.geant4.org/geant4/

[15] L. J. Meng, and D. K. Wehe, "Feasibility study of using hybrid collimation for nuclear environmental imaging," *IEEE Trans. Nucl. Sci.*, vol. 50, no. 4, pp. 1103-1110, August, 2003.

[16] L. J. Meng, N. H. Clinthorne, S. Skinner, R. V. Hay, and M. Gross, "Design and feasibility study of a single photon emission microscope system for small animal I-125 imaging," *IEEE Trans. Nucl. Sci.*, vol. 53, pp. 1168-1178, 2006.

[17] L. J. Meng, W. L. Rogers, N. H. Clinthorne et al., "Feasibility study of Compton scattering enchanced multiple pinhole imager for nuclear medicine," *IEEE Trans. Nucl. Sci.*, vol. 50, no. 5, pp. 1609-1617, October, 2003.

[18] L. J. Meng, G. Fu, J. W. Tan, C. T. Chen, "Imaging Performance of an Sub-Hundred Micron Resolution Spect/Ct System", Presented In IEEE NSS/MIC 2007, Hawaii.

[19] L. J. Meng, and N. H. Clinthorne, "A modified uniform Cramer-Rao bound for multiple pinhole aperture design," *IEEE Trans. Med. Imaging*, vol. 23, no. 7, pp. 896-902, July, 2004.

[20] L. J. Meng and Nan Li, "A Vector Uniform Cramer-Rao Bound for SPECT System Design", to appear in *IEEE Trans. Nucl. Sci.*

[21] J. A. Fessler and W. L. Rogers, "Spatial resolution properties of penalized-likelihood image reconstruction: Space-invariant tomographs," *IEEE Trans. on Image Processing*, vol. 5, pp. 1346-1358, 1996.

[22] L. J. Meng and G. Fu, "Investigation of the Intrinsic Spatial Resolution of an Intensified EMCCD Scintillation Camera", to appear in *IEEE Trans. Nucl. Sci.*

What is claimed is:

1. An apparatus, comprising:
an X-ray source that generates a plurality of modes of an X-ray beam, each mode of the plurality of modes having different geometries;
a collimator positioned next to a compound, wherein the collimator has at least one aperture, wherein the compound emits fluorescence X-rays when impacted by the X-ray beam generated by the X-ray source in a specific one of the plurality of modes of the X-ray beam, wherein the collimator comprises a material that absorbs at least a first portion of the fluorescence X-rays emitted by the compound and releases at least a second portion of the fluorescence X-rays at the at least one aperture, wherein the second portion of the fluorescence X-rays released by the at least one aperture have known directional information based on a position of the collimator; and
a fluorescence detector for detecting the second portion of the fluorescence X-rays released by the at least one aperture, wherein a first mode of the X-ray beam provides a first instance of the second portion of the fluorescence X-rays for defining regions-of-interest of the compound, and wherein a second mode of the X-ray beam provides one or more additional instances of the second portion of the fluorescence X-rays for generating a three-dimensional (3-D) rendering of an elemental distribution of the compound determined from a combination of the first instance and the one or more additional instances of the fluorescence X-rays detected and the known directional information of the collimator.

2. The apparatus of claim 1, wherein the X-ray source is a synchrotron.

3. The apparatus of claim 1, wherein at least a portion of the at least one aperture is covered with gold, tungsten, lead, depleted uranium, or combinations thereof.

4. The apparatus of claim 1, wherein the at least one aperture comprises one of a slit opening, a circular opening, a rectangular opening, and concentric ring openings.

5. The apparatus of claim 1, wherein the fluorescence detector comprises one of a charge coupled device detector, a complementary metal-oxide-semiconductor detector, a double sided silicon strip detector, or a silicon strip detector.

6. The apparatus of claim 1, comprising a controller that executes instructions and performs operations comprising:
receiving detection data from the one or more fluorescence detectors; and
determining the 3-D rendering of the elemental distribution of the compound from the detection data and the directional information associated with the fluorescence X-rays emitted by the at least one aperture.

7. The apparatus of claim 6, wherein the controller further performs operations comprising determining from the detection data an energy of the fluorescence X-rays emitted by the at least one aperture.

8. The apparatus of claim 1, wherein a first mode of the plurality of modes of the X-ray beam emitted by the X-ray source comprises a thin slice X-ray beam.

9. The apparatus of claim 1, wherein a first mode of the plurality of modes of the X-ray beam emitted by the X-ray source comprises an extended square X-ray beam.

10. A method, comprising:
applying a first mode of a plurality of modes of an X-ray beam to an object;
applying a second mode of the plurality of modes of the X-ray beam to the object;
receiving fluorescence X-rays responsive to the first mode and the second mode of the X-ray beam impacting the object, wherein the fluorescence X-rays have known directional information, wherein the first mode of the X-ray beam provides a first instance of the fluorescence X-rays for defining regions-of-interest of the object, and wherein the second mode of the X-ray beam provides one or more additional instances of the fluorescence X-rays for generating a three-dimensional (3-D) rendering of an elemental distribution of the object determined from a combination of the first instance and the one or more additional instances of the fluorescence X-rays and the known directional information of the fluorescence X-rays;
measuring energy from the fluorescence X-rays; and
constructing the 3-D rendering of the elemental distribution of the object according to the measured energy of the fluorescence X-rays and their corresponding directional information.

11. The method of claim 10, wherein the X-ray beam is generated by one of a synchrotron X-ray source, or a non-synchrotron X-ray source.

12. The method of claim 10, wherein the fluorescence X-rays are released by a plurality of apertures in each of a plurality of collimators surrounding the object.

13. The method of claim 12, wherein the plurality of apertures comprise a plurality of slits, circular holes, rectangular holes, or concentric ring openings.

14. The method of claim 10, comprising detecting the fluorescence X-rays with a plurality of fluorescence detectors surrounding a corresponding plurality of collimators.

15. The method of claim 14, wherein each of the plurality of fluorescence detectors comprises one of a charge coupled device detector, a complementary metal-oxide-semiconductor detector, a double sided silicon strip detector, and a silicon strip detector.

16. The method of claim 10, wherein the X-ray beam comprises one of a thin slice X-ray beam, and an extended square X-ray beam.

17. A computer-readable storage medium, comprising computer instructions, which when executed by a processor cause the processor to perform operations comprising:
measuring energy from fluorescence X-rays emitted by a compound impacted by an X-ray beam responsive to a first application of a first mode of a plurality of modes of the X-ray beam and a second application of a second mode of the plurality of modes of the X-ray beam, wherein the fluorescence X-rays have known directional information, wherein the first mode of the X-ray beam provides a first instance of the fluorescence X-rays for defining regions-of-interest of the compound, and wherein the second mode of the X-ray beam provides one or more additional instances of the fluorescence X-rays for generating a three-dimensional (3-D) rendering of an elemental distribution of the compound determined from a combination of the first instance and the one or more additional instances of the fluorescence X-rays and the known directional information of the fluorescence X-rays; and constructing the 3-D rendering of the elemental distribution of the compound according to the measured energy of the fluorescence X-rays and their corresponding directional information.

18. The storage medium of claim 17, wherein the fluorescence X-rays are released by a plurality of apertures in each of a plurality of collimators surrounding the compound.

19. The storage medium of claim 17, wherein measuring the energy of the fluorescence X-rays comprises measuring the energy of the fluorescence X-rays from data supplied by a plurality of fluorescence detectors surrounding a corresponding plurality of collimators.

20. The storage medium of claim 19, wherein each of the plurality of fluorescence detectors comprises one of a charge coupled device detector, a complementary metal-oxide-semiconductor detector, a double sided silicon strip detector, or a silicon strip detector.

* * * * *